(12) United States Patent  
Osetek et al.

(10) Patent No.: US 9,781,954 B1
(45) Date of Patent: Oct. 10, 2017

(54) BRA WITH WARMER POCKETS

(71) Applicants: Amy Osetek, Center Conway, NH (US); Daniel Osetek, Center Conway, NH (US); Linda A. Prushinski, Intervale, NH (US)

(72) Inventors: Amy Osetek, Center Conway, NH (US); Daniel Osetek, Center Conway, NH (US); Linda A. Prushinski, Intervale, NH (US)

(*) Notice: Subject to any disclaimer, the term of this patent is extended or adjusted under 35 U.S.C. 154(b) by 0 days.

(21) Appl. No.: 15/457,652

(22) Filed: Mar. 13, 2017

(51) Int. Cl.
*A41C 3/00* (2006.01)
*A61F 7/02* (2006.01)
*A61F 7/00* (2006.01)

(52) U.S. Cl.
CPC .......... *A41C 3/0035* (2013.01); *A41C 3/0057* (2013.01); *A61F 7/02* (2013.01); *A61F 2007/0021* (2013.01); *A61F 2007/0234* (2013.01); *A61F 2007/0238* (2013.01)

(58) Field of Classification Search
CPC .. A41C 3/00; A41C 3/10; A41C 3/148; A41C 3/0035; A41C 3/04
USPC ......................... 450/36, 89, 54–57
See application file for complete search history.

(56) References Cited

U.S. PATENT DOCUMENTS

| | | | | |
|---|---|---|---|---|
| 2,568,175 A * | 9/1951 | Ullrich | ..................... | A41C 3/10 2/267 |
| 4,699,144 A * | 10/1987 | Sherwood | .............. | A41C 3/148 450/54 |
| 5,098,330 A * | 3/1992 | Greenberg | ............... | A41C 3/10 450/31 |
| 5,334,082 A * | 8/1994 | Barker | ..................... | A41C 3/10 2/247 |
| 6,088,942 A * | 7/2000 | Brooks | ............... | G09F 15/0025 160/328 |
| 6,443,805 B1 * | 9/2002 | Kirkwood | ............ | A41C 3/0035 450/31 |
| 6,464,717 B1 * | 10/2002 | Smith | ....................... | A61F 7/02 450/58 |
| 7,081,034 B1 * | 7/2006 | Zoellner | .................. | A41C 3/04 2/104 |
| 7,309,275 B1 * | 12/2007 | Morales | .................... | A41C 3/02 450/38 |
| 8,597,072 B1 * | 12/2013 | Lucas | .................. | A41C 3/0035 2/247 |
| 2006/0265060 A1 * | 11/2006 | Stelter | ..................... | A41C 3/148 623/7 |
| 2007/0270078 A1 * | 11/2007 | Henry | .................. | A41C 3/0035 450/54 |
| 2009/0209173 A1 * | 8/2009 | Arledge | ............... | A41C 3/0035 450/39 |
| 2011/0092134 A1 * | 4/2011 | Alva | ........................ | A41C 3/04 450/36 |
| 2013/0143469 A1 * | 6/2013 | Grippaudo | ............. | A41C 3/148 450/3 |

* cited by examiner

*Primary Examiner* — Gloria Hale
(74) *Attorney, Agent, or Firm* — Michael J. Persson; Catherine Napjus; Lawson Persson & Chisholm

(57) ABSTRACT

A bra including a front with a right cup, a left cup, a right strap, and a left strap, at least one pocket in each of the right and left cups that are shaped and dimensioned to accept warming inserts, a back, and sides connecting the right cup to the back and the left cup to the back.

19 Claims, 2 Drawing Sheets

BRA WITH WARMER POCKETS

FIELD OF THE INVENTION

The present invention relates to foundation garments, and in particular, to sports bras with inserts for warmers.

BACKGROUND

Sports bras are available in a variety of styles and materials. They are designed to provide increased levels of support as well as comfort during exercise. In many cold-weather outdoor activities, such as skiing, ice skating, snowmobiling, ice hockey, etc., it is a common complaint that the wearer's core body and breasts become cold.

A number of patents have addressed the need for a bra that warms or cools a wearer's breasts. For example, U.S. Pat. Nos. 5,235,974 and 9,364,030 each disclose bras with electrical heating elements. These bras effectively work the breast of the user but each has significant drawbacks. First, each requires the use of wires through the cup area, which is uncomfortable to the user when engaging in outdoor activities. Second, the need for battery power means that the bra will be heated for a limited duration and cannot be effectively re-heated once the battery is dead.

Some patents have used inserts to heat or cool a bra. For example, U.S. Pat. No. 6,464,717 discloses a bra with hot/cold inserts. This bra takes the form of a thermal vest that includes pockets on the interior thereof into which hot or cold inserts may be inserted. Although this bra addresses some of the drawbacks of electrically heated bras, it also has significant drawbacks. In particular, the inclusion of pockets on the inside of the bra requires the wearer to completely disrobe in order to place an insert in the pocket. Further, as the insert is placed in the pocket when the bra is not fastened to the wearer, the wearer cannot be assured that the insert is in a comfortable position and cannot easily reposition the insert to such a position.

Finally, U.S. Pat. No. 7,275,977 discloses a therapeutic bra for use by women who have recently undergone breast surgery, which includes a single pocket on the outside of the bra into which a wearer may insert a hot or cold pack. This patent overcomes the drawback of having an interior pocket. However, the use of a single pocket on the top of the bra prevents the insert from being positioned to heat the underside of the breast, does not allow the inserts to be comfortably positioned and allows the insert to move within the pouch when the user engages in physical activity.

Therefore there is a need for a sports bra to be able to warm the wearer's core body and breasts that does not require the use of electrical wires or batteries, that may be easily reheated without removing the bra, that allows heating inserts to be easily positioned for comfort and heating of desired parts of the breast, and that prevents the insert from moving within the pouch when the user engages in physical activity

SUMMARY OF THE INVENTION

The present invention is a bra and a bra kit.

In its most basic form, the bra of the present invention includes a front with a right cup, a left cup, a right strap, and a left strap, at least one pocket in each of the right and left cups, inserts for the pockets, a back, and sides connecting the right cup to the back and the left cup to the back.

The bra of the present invention may be any type of bra that includes right and left cups, a back, and sides, but is preferably a sports bra-type bra. As used herein, the term "sports bra-type bra" refers to bras commonly worn by women engaging in high-impact activities. Sports bra-type bras typically provide increased support for and motion limitation of the breasts of the wearer. Sports bra-type bras also typically have larger cups, backs, and sides than regular bras, therefore covering more of the wearer than a regular bra. One of ordinary skill in the art will understand these distinctions between sports bra-type bras and regular bras. As used herein "cups" refers generally to the right and left sides of the front of the bra. Many bras include cups, as more traditionally understood in the context, which are rounded structures sized and dimensioned to support the wearer's breast. These cups are "cups" as contemplated within the context of the present invention. Many sports-bra type bras do not include such traditional cups, however, but do always include some sort of covering on the right and left sides of the front of the bra. Such coverings are also included within the term "cup" as used herein.

Each cup of the bra includes at least one pocket. The pocket may be on the interior of the cup, such that the pocket is disposed directly against the wearer's skin. The pocket may be on the exterior of the cup, such that the material of the cup is between the wearer's skin and the pocket. If the cups include at least two layers of material, the pocket may be disposed between the layers of material. Similarly, if the cups include at least two layers of material, the pocket may be formed by the at least two layers of the material. This is accomplished by attaching the layers of material to one another in the shape of the pocket, by stitching, gluing, or other permanent delineation.

At least one side of each of the pockets includes an opening on the exterior of the bra that allows the insert to be removed and replaced. In the preferred embodiment, each cup includes a single pocket having both a top opening and a side opening. This is preferred as it allows the wearer to easily position the insert within the pocket. However, it is understood that pockets may be located anywhere on the cup. In some embodiments, each cup includes a single pocket having a single opening. In other embodiments, each cup includes two pockets for inserts. In embodiments that include two pockets on each cup, it is preferred that one pocket be located on the cup toward the side of the bra and one pocket be located on the top of the cup.

It is preferred that each pocket also include some means for partially or totally closing the opening, such as by hook and eye fastener, a button, compression, or some other means. In addition, it is preferred that the pockets provide not only sufficient room for the inserts, but also some amount of sufficient room for the inserts to be manipulated and adjusted by hand within the pocket.

As the preferred inserts are air activated warmers, as discussed below, it is preferred that each opening into the pockets be sized to accommodate such warmers. One of ordinary skill in the art will recognize, however, that the sizes and shapes of the pockets may vary widely, and may depend on factors such as the type, size, and shape of the insert used, the type of bra, the size and shape of the cups, and/or how the pocket is formed in the cup.

The inserts of the present invention are heat-emitting. As used herein, the term "heat-emitting" means that the inserts actually emit heat. That is to say, the inserts do not provide additional heat for the wearer merely by virtue of being another layer of material between the wearer's skin and the elements. The inserts are preferably "warmers." As used herein, the term "warmer" specifically refers to packets containing reagents that produce an exothermic reaction subtle enough to occur safely in close proximity to the skin, but powerful enough to be felt through the packet in which the reagents are held. The preferred warmer is a common type of warmer that is air activated, where the packet contains, for example, cellulose, iron, water, activated carbon, vermiculite, and salt, and produces heat from the exothermic oxidation of iron when exposed to air. These types of warmers are typically not reusable, as they will cease to emit heat once the iron in the packet is fully oxidized. Common examples of warmers of this type include those sold under the trademarks GRABBER and HOTHANDS. Other warmers generate heat through the exothermic crystallization or supersaturated solutions (typically sodium acetate) and are usually reusable by immersing the warmer in very hot water. Other types of warmers may include those fueled by lighter fluid, batteries, or charcoal. The warmers discussed above are merely exemplary and should not be considered an inclusive list of the possibility of warmers that may be used as inserts in the present invention. The inserts of the present invention may also be small reusable heating pads filled with a material with a high specific heat capacity that may be heated before use within the present invention.

It is preferred that at least the cups of the bra be made of a flexible, heat resistant material, such as nylon, spandex, lycra, elastane, cotton, polyester blend, and merino wool, or some combination thereof. It is understood that this is a preferred, but non-exclusive list of such heat resistant materials. As the cups will be need to maintain functionality and longevity even while being subjected to the emitted heat of the inserts, the heat resistance is important.

The kit of the present invention includes a bra and at least two inserts. The bra is any of those described above, so long as the pockets are such that an insert may be inserted into and removed from the pockets. The inserts are any of those described above Therefore, it is an aspect of the invention to provide a sports bra capable of warming the wearer's core body and breasts that does not require the use of electrical wires or batteries.

It is a further aspect of the invention to provide a sports bra capable of warming the wearer's core body and breasts that may be easily reheated without removing the bra.

It is a further aspect of the invention to provide a sports bra capable of warming the wearer's core body and breasts that allows heating inserts to be easily positioned for comfort and heating of desired parts of the breast.

It is a still further aspect of the invention to provide a sports bra capable of warming the wearer's core body and breasts that prevents the insert from moving within the pouch when the user engages in physical activity.

These aspects of the present invention are not meant to be exclusive and other features, aspects, and advantages of the present invention will be readily apparent to those of ordinary skill in the art when read in conjunction with the following description and accompanying drawings.

DETAILED DESCRIPTION

Figure 1A:
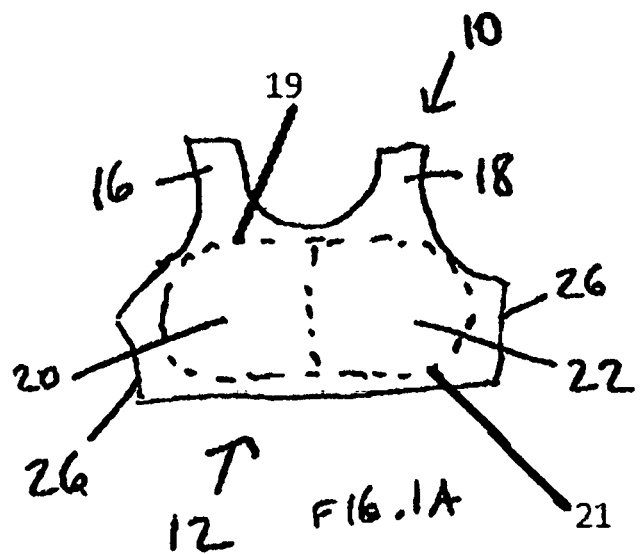
FIG. 1A is a front view of the front of a bra of the present invention.
Figure 1B:
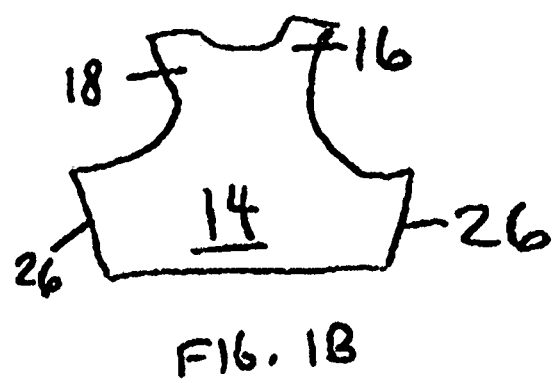
FIG. 1B is a front view the back of a bra of the present invention.

Referring first to FIGS. 1A and 1B, views of the front and back of a bra 10 of the present invention are provided, respectively. The bra 10 is a sports bra-type bra, as is preferred, but it is understood that any bra may be used with the present invention. Bra 10 has front 12, back 14, and sides 26. Front 12 has right and left straps 16, 18 and right and left cups 20, 22. Right and left straps 16, 18 connect front 12 directly with back 14. Sides 26 connect the sides of front and back 12, 14. Perimeters 19, 21 of cups 20, 22 are indicated in dotted lines in FIG. 1A. It is understood, however, that cups 20, 22 are integrated into front 12, so no such delineation may be visible. The size and shape of cups 20, 22 may vary, but there general placement within front 12 is as shown.

Figure 2A:
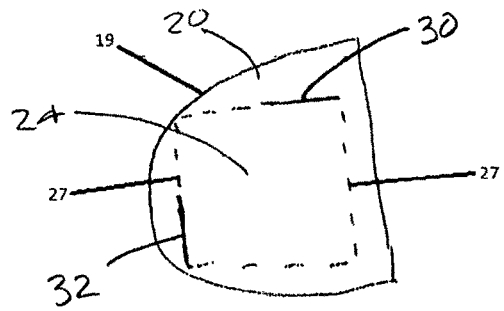
FIG. 2A is an isolated view of a right cup of the preferred bra of the present invention.

Now referring to FIG. 2A, a view of right cup 20 is provided in isolation. Top opening 30 and side opening 32 of pocket 24 are shown in solid lines and the reminder of pocket 24 is shown in dotted lines. Top opening 30 and side opening 32 pass through the exterior of the cup 20 and are each sized to accept an insert 28, such as the insert 28 shown in FIG. 2B. The inclusion of both a top opening 30 and a side opening 32 is preferred, as it allows the wearer to easily position the insert 28 within the pocket 24 for desired heating and comfort. It is understood, however, that the openings 30, 32 may be positioned anywhere on the cup 20, 22. Although only right cup 20 is shown in FIG. 2A, it is understood that left cup 22 would be a mirror image of that shown in FIG. 2A.

In the embodiment of FIG. 2A, pocket 24 with edges 27 is disposed on the interior of the cup 20, such that the pocket 24 is disposed directly against the wearer's skin and openings 30, 32 pass through the exterior of the cup 20. Edges 27 are disposed completely within perimeter 19 of cup 20. That is to say, as far as area of the respective materials of pocket 24 and cup 20, the area of the material of pocket 24 fits entirely within the area of the material of cup 20 so that pocket 24 and cup 20 share no seams or edges. This arrangement is shown in detail in FIG. 3. In this arrangement, the cup 20 includes outer surface 23 and inner surface 25. Top opening 30 and side opening (not shown) pass though the cup 20. Pocket 24 is formed by attaching an inner layer 40 of material to the inner surface 25 of the cup 20. In use, the insert 28 is passed through top opening 30 or side opening (not shown) and is positioned within the pocket 24 by the user. Inner layer 40 may be formed from many types of material, including polypropylene fleece, provided such material provides comfort and allows heat to pass there through. As bra 10 will need to withstand the heat emitted by inserts 28, it is preferred that at least cups 20, 22 be made of a flexible, heat resistant material, such as nylon, spandex, lycra, elastane, cotton, polyester blend, and merino wool, or a combination thereof.

Figure 3:
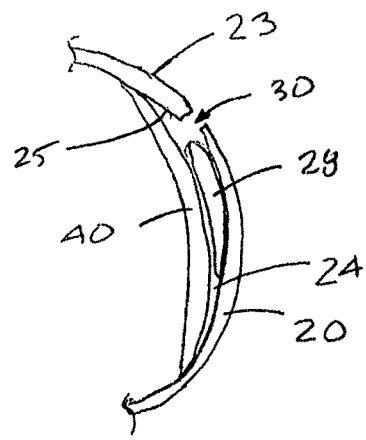
FIG. 3 is a section view of the preferred bra showing the position of the pocket and insert within the cup.

It is noted that, although the pocket 24 in FIG. 3 is shown on the interior of the cup 20, it may also be formed by adding the inner layer 40 to the outer surface 23 of the cup 20. In such embodiments, it is preferred that the inner layer 40 be made of a material that compresses the insert and holds it in place within the pocket 24. Regardless of where the pocket 24 is disposed, it is attached to the cup 20 by attaching the layers of material to one another by stitching, gluing, or other permanent delineation. Given each and any of these possibilities for the formation of pocket 24 within cup 20, pocket 24 may or may not be visible on cup 20, but the dotted lines indicate a position of pocket 24 within cup 20.

Figure 2B:
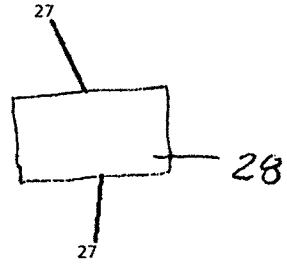
FIG. 2B is an isolated view of an insert that may be inserted into the right cup of the preferred bra of FIG. 2A.

Now referring to FIG. 2B, an exemplary insert 28 is shown. Inserts 28 are sized and dimensioned to be insertable and removable from pockets 24, as shown in FIG. 2A. The inserts 28 shown are the preferred warmers, as discussed above.

Figure 4A:
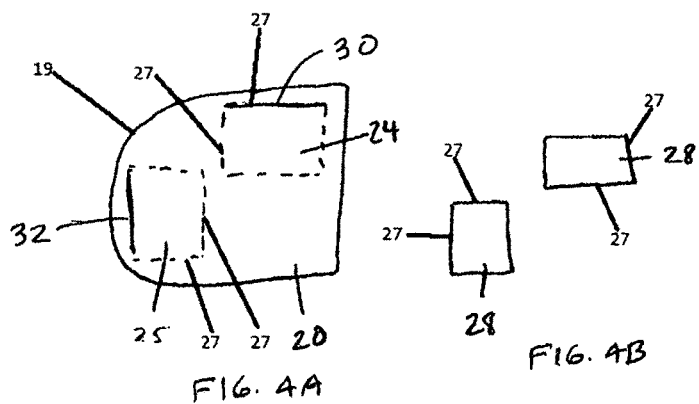
FIG. 4A is an isolated view of a right cup of an alternative embodiment of the bra of the present invention having two pockets in each cup.
Figure 4B:
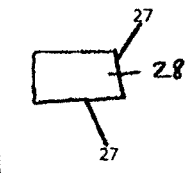
FIG. 4B is an isolated view of two inserts that may be inserted into the two pockets of the right cup of the bra of FIG. 3A.

Referring now to FIGS. 4A and 4B, a cup 20 in accordance with an alternative embodiment of the invention is shown. In this cup, two pockets 24, 25 are provided within the cup 20. Top opening 30 is in communication with top pocket 24 and side opening 32 is in communication with side pocket 25. In such embodiments, two inserts 28, such as those shown in FIG. 4B are used with a single insert 28 inserted into each of pockets 24, 25. Similar to that shown in FIGS. 2A and 2B, pockets 24, 25 have edges 27 that are disposed completely within perimeter 19 of cup 20 such that pockets 24, 25 share no edges or seams with cup 20.

Although the present invention has been described in considerable detail with reference to certain preferred versions thereof, other versions would be readily apparent to those of ordinary skill in the art. Therefore, the spirit and scope of the description should not be limited to the description of the preferred versions contained herein.

What is claimed is:

1. A bra, comprising:
   a right cup sized and dimensioned to support a right breast of a wearer of said bra;
   a left cup attached to said right cup, wherein said left cup is sized and dimensioned to support a left breast of the wearer of said bra, and wherein each of said right cup and said left cup comprises a perimeter;
   an inner layer of material forming a pocket within each of said right cup and said left cup, wherein edges of said material are disposed completely within said perimeters of said right and left cups;
   a top opening and a side opening disposed through said right cup and a top opening and a side opening disposed through said left cup;
       wherein said top opening and said side opening through said right cup are in communication with said pocket within said right cup and said top opening and said side opening through said left cup are in communication with said pocket within said left cup; and
       wherein each of said top openings and side openings are shaped and dimensioned to allow a heat-emitting insert to pass into and be held within each of said pockets;
   a front comprising said right and left cups and left and right straps;
   a back that covers at least a portion of a back of the wearer of said bra, wherein said left and right straps of said front connect with said back; and
   two sides, one of which connects said right cup to said back and one of which connects said left cup to said back.

2. The bra as claimed in claim 1, wherein said bra is a sports bra-type bra.

3. The bra as claimed in claim 1, wherein said inserts are warmers.

4. The bra as claimed in claim 1, wherein each of said right cup and said left cup comprises two pockets and said bra comprises four inserts.

5. The bra as claimed in claim 1, wherein at least said right cup and said left cup of said bra are made of a flexible and heat resistant material.

6. The bra as claimed in claim 5, wherein said flexible and heat resistant material is one or a combination of at least two of a group consisting of nylon, spandex, elastane, cotton, polyester blend, and merino wool.

7. The bra as claimed in claim 1, wherein said inner layer of material comprises a layer of polypropylene fleece.

8. A bra kit, comprising:
   a bra, comprising:
       a right cup sized and dimensioned to support a right breast of a wearer of said bra;
       a left cup attached to said right cup, wherein said left cup is sized and dimensioned to support a left breast of the wearer of said bra, and wherein each of said right cup and said left cup comprises a perimeter;
       an inner layer of material forming a pocket within each of said right cup and said left cup, wherein edges of said material are disposed completely within said perimeters of said right and left cups;
       a top opening and a side opening disposed through said right cup and a top opening and a side opening disposed through said left cup;
           wherein said top opening and said side opening through said right cup are in communication with said pocket within said right cup and said top opening and said side opening through said left cup are in communication with said pocket within said left cup; and
           wherein each of said top openings and side openings are shaped and dimensioned to allow a heat-emitting insert to pass into and be held within each of said pockets;
       a front comprising said right and left cups and left and right straps;
       a back that covers at least a portion of a back of the wearer of said bra, wherein said left and right straps of said front connect with said back; and
       two sides, one of which connects said right cup to said back and one of which connects said left cup to said back; and
   at least two heat-emitting inserts sized and dimensioned to fit within said pockets of said right cup and said left cup, wherein said inserts provide an additional layer for warmth of the breasts of the wearer.

9. The bra kit as claimed in claim 8, wherein said bra is a sports bra-type bra.

10. The bra kit as claimed in claim 8, wherein said inserts are warmers.

11. The bra kit as claimed in claim 8, wherein each of said right cup and said left cup comprises two pockets and said bra comprises four inserts.

12. The bra kit as claimed in claim 8, wherein at least said right cup and said left cup of said bra are made of a flexible and heat resistant material.

13. The bra kit as claimed in claim 12, wherein said flexible and heat resistant material is one or a combination of at least two of a group consisting of nylon, spandex, elastane, cotton, polyester blend, and merino wool.

14. A bra, comprising:
   a right cup sized and dimensioned to support a right breast of a wearer of said bra;
   a left cup attached to said right cup, wherein said left cup is sized and dimensioned to support a left breast of the wearer of said bra, and wherein each of said right cup and said left cup comprises a perimeter;
a layer of material forming a pocket on the outer surface of each of said right cup and said left cup, wherein edges of said material are disposed completely within said perimeters of said right and left cups;
a top opening and a side opening formed between said layer of material and said right cup and a top opening and a side opening formed between said layer of material and said left cup;
   wherein said top opening and said side opening formed on said right cup are in communication with said pocket on said outer surface of said right cup and said top opening and said side opening formed on said left cup are in communication with said pocket on said outer surface said left cup; and
   wherein each of said top openings and side openings are shaped and dimensioned to allow a heat-emitting insert to pass into and be held within each of said pockets;
a front comprising said right and left cups and left and right straps;
a back that covers at least a portion of a back of the wearer of said bra, wherein said left and right straps of said front connect with said back; and
two sides, one of which connects said right cup to said back and one of which connects said left cup to said back.

15. The bra as claimed in claim 14, wherein said bra is a sports bra-type bra.

16. The bra as claimed in claim 14, wherein said inserts are warmers.

17. The bra as claimed in claim 14, wherein each of said right cup and said left cup comprises two pockets and said bra comprises four inserts.

18. The bra as claimed in claim 14, wherein at least said right cup and said left cup of said bra are made of a flexible and heat resistant material.

19. The bra as claimed in claim 18, wherein said flexible and heat resistant material is one or a combination of at least two of a group consisting of nylon, spandex, elastane, cotton, polyester blend, and merino wool.

\* \* \* \* \*